(12) United States Patent
Pell, Jr. et al.

(10) Patent No.: US 6,472,557 B1
(45) Date of Patent: Oct. 29, 2002

(54) PROCESS FOR RECYCLING POLYESTERS

(75) Inventors: Thomas Michael Pell, Jr., Kingsport, TN (US); Michael Paul Ekart, Wassenaar (NL); David Dunlap Cornell, Kingsport, TN (US); Damon Brian Shackelford, Johnson City, TN (US); Donald Lee Carver, Church Hill, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/438,859

(22) Filed: Nov. 12, 1999

Related U.S. Application Data
(60) Provisional application No. 60/119,529, filed on Feb. 10, 1999.

(51) Int. Cl.$^7$ .......................... C07C 51/00; C07C 67/48; C07C 67/00
(52) U.S. Cl. ............................ 562/483; 560/78; 560/89; 560/96
(58) Field of Search ............................ 562/483; 560/78, 560/89, 96

(56) References Cited

U.S. PATENT DOCUMENTS

| | | |
|---|---|---|
| 3,037,050 A | 5/1962 | Heisenberg et al. |
| 3,321,510 A | 5/1967 | Lotz et al. |
| 3,488,298 A | 1/1970 | Barkey et al. |
| 3,776,945 A | 12/1973 | Ligorat et al. |
| 4,064,112 A | 12/1977 | Rothe et al. |
| 4,163,860 A | 8/1979 | Delattre et al. |
| 4,302,595 A | 11/1981 | Schoengen et al. |
| 4,578,501 A | 3/1986 | Schoengen et al. |
| 4,620,032 A | 10/1986 | Doerr |
| 4,642,377 A | 2/1987 | Modic et al. |
| 5,051,528 A | 9/1991 | Naujokas et al. |
| 5,298,530 A | 3/1994 | Gamble et al. |
| 5,338,882 A | 8/1994 | Korte et al. |
| 5,414,022 A | 5/1995 | Toot, Jr. et al. |
| 5,432,203 A | 7/1995 | DeBruin et al. |
| 5,576,456 A | 11/1996 | Gamble et al. |
| 5,679,848 A | 10/1997 | Korte et al. |
| 5,770,778 A | 6/1998 | Naujokas |
| 5,821,381 A | 10/1998 | Naujokas |

FOREIGN PATENT DOCUMENTS

| | | |
|---|---|---|
| EP | 0 662 466 A1 | 7/1995 |
| EP | 0 484 963 A2 | 5/2002 |
| WO | WO95/01954 A1 | 1/1995 |
| WO | WO95/27753 A1 | 10/1995 |

*Primary Examiner*—Paul J. Killos
(74) *Attorney, Agent, or Firm*—Dennis Carmen; Bernard J. Graves, Jr.

(57) ABSTRACT

A process for producing high quality TPA suitable for PET feedstock material from recycled polyester. The process includes the steps of depolymerizing the polyester to form DMT; separating the DMT from secondary materials; and hydrolyzing the DMT to form TPA. In a preferred embodiment of the invention the recycled polyester is contacted with a component monomer or oligomer thereof to liquefy the polyester prior to depolymerizing the polyester.

23 Claims, 1 Drawing Sheet

PROCESS FOR RECYCLING POLYESTERS

CROSS-REFERENCE TO RELATED APPLICATION

This application claims benefit to the provisional application filed Feb. 10, 1999, having U.S. Ser. No. 60/119,529, the disclosure of which is incorporated herein by reference.

FIELD OF THE INVENTION

This invention relates to polyesters and more particularly to an improved process for recycling polyesters. The improved process requires little purification equipment and can handle variable post consumer feedstock or other recyclable polyester materials besides polyethylene terephthalate (PET). More particularly, this invention relates to the recycling of PET, and the production of terephthalic acid (TPA) therefrom.

BACKGROUND OF THE INVENTION

Polyester resins have widespread utility in a variety of applications, such as films, thermoforming, and blow molding. Additionally, polyesters have widespread acceptance and use in today's consumer products. Polyesters, such as PET and polyethylene naphthalate (PEN), are used in single and multiple use products such as food and beverage contains, and especially carbonated drink containers, photographic film, magnetic tape, and the like.

In an effort to conserve resources, several methods have been disclosed in the literature for recycling polyesters. Some methods involve depolymerization, i.e., breaking the ester bond and reducing the polymer to its monomer components. Others processes blend virgin polymer with post-consumer materials. These latter processes tend to be simpler and the equipment is less expensive. However, these simpler processes are not without their problems. These processes cannot remove many of the variable constituents, such as colorants and catalyst metals, present in post-consumer polyesters.

Depolymerization of post-consumer polyester into its monomeric components offers more promise since the monomers can in some cases be purified by techniques well known in the art such as distillation, crystallization and filtration. The pure recycle monomers can subsequently be fed to a polyester production process. The cost of the purification steps, however, can make the recycle monomers more expensive than virgin raw materials.

Various methods have been disclosed in the literature for depolymerization of post-consumer polyesters into their component monomers, such as ethylene glycol and terephthalic acid, naphthalene dicarboxylic acid or their derivatives, so they could be reused.

For example, U.S. Pat. No. 3,037,050 discloses the recovery of terephthalate acid dimethyl ester by treating polyethylene terephthalate in the form of bulky or lumpy solid masses with super-heated methanol vapor in the presence of any suitable transesterification catalyst substantially at atmospheric pressure.

U.S. Pat. No. 3,321,510 discloses a process for decomposing polyethylene terephthalate by treating with steam at a temperature of from about 200° C. to 450° C. The steam-treated polyethylene terephthalate is then reduced from a brittle solid product to a powder having a mean particles size of from about 0.0005 to 0.002 millimeters, after which the fine powder is atomized with a gaseous substance including inert gas and methanol vapor to form an aerosol. The aerosol is conducted through a reaction zone at a temperature of 250° C. to 300° C. in the presence of excess methanol vapors.

U.S. Pat. No. 3,776,945 discloses a process of depolymerizing polyethylene terephthalate waste to obtain dimethyl terephthalate and ethylene glycol. The waste is sub-divided into dimensions between 4 and 35 mesh and treated at a temperature of 100° C. to 300° C. in the presence of acid catalysts. The proportion of methanol to waste is between 1:1 and 10:1 by weight.

U.S. Pat. No. 4,302,595 discloses an integrated multi-stage process which involves production of a crude ester mixture containing DMT, distillation of the crude ester to produce a crude DMT substantially free of interfering impurities such as terephthalaldehydic acid methyl ester, hydrolysis of the crude DMT in at least two stages to produce TPA and recovery of a purified TPA as well as recovery of methanol.

A crude ester mixture containing DMT is produced by oxidizing p-xylene of technical purity and preferably a mixture of p-xylene and methyl p-toluate with gases containing molecular oxygen in the presence of an oxidation catalyst which contains cobalt and can contain a mixture of cobalt and manganese.

U.S. Pat. No. 4,578,501 discloses a process for the production of fiber grade terephthalic acid from dimethyl terephthalate as the intermediate product by oxidation of p-xylene and/or methyl p-toluate with oxygen-containing gases in the presence of heavymetal-containing oxidation catalysts at elevated temperature and elevated pressure by esterification of the oxidation mixture with methanol at elevated temperature and elevated pressure and by distillatory separation of the crude ester into a methyl p-toluate-rich fraction to be recycled into the oxidation reactor and a residual fraction as well as a crude dimethyl terephthalate having a limited content of oxidation intermediates and other by-products, by continuous hydrolysis of the crude dimethyl terephthalate with water at a mass ratio of crude dimethyl terephthalate to water of between 3:1 and 0.1:1 and at a temperature of between 140° C. and 350° C. and at a pressure required to maintain the liquid phase to produce a reaction mixture containing crystalline fiber grade terephthalic acid, by recrystallization of the terephthalic acid.

U.S. Pat. No. 4,620,032 teaches an extrusion process for reducing the reaction time in the hydrolysis of polyesters by intimately admixing with the molten polyester a depolymerizing agent which is either one of the products resulting from the complete hydrolytic depolymerization of the polyester or water.

U.S. Pat. No. 5,051,528 discloses a method for recovering ethylene glycol and dimethyl terephthalate (DMT) from polyethylene terephthalate polymers (PET). The process includes the steps of dissolving scrap polyester in oligomers of ethylene glycol and terephthalate acid or dimethyl terephthalate and passing super-heated methanol through the solution. The ethylene glycol and dimethyl terephthalate are subsequently recovered overhead.

U.S. Pat. No. 5,298,530 discloses a process of recovering components from PET having the steps of introducing glycol and terephthalic acid or dimethyl terephthalate oligomers to a first vessel and heating the oligomers, introducing scrap polyesters to the first vessel and forming a start-up melt with the oligomers, transferring the melt from the first vessel to a second vessel, passing super-heated methanol through the melt in the second vessel to form a final melt comprising low molecular weight polyesters in monomers, transferring the final melt from the second vessel to the first vessel, and recovering components in the form of a vapor stream exiting the second vessel. The process shortens the length of the polyester chain in a polyester scrap melt prior to the introduction of the scrap melt to a depolymerization reactor.

U.S. Pat. No. 5,414,022 discloses an improvement to the process of U.S. Pat. No. 5,051,528. The improvement includes the steps of adding polyester to the dissolver and combining it with melt from the reactor and liquid from the rectifier to reduce the chain length of the polyester, transferring the reduced chain length polyester from the dissolver to the reactor, passing super-heated methanol through the reactor to depolymerize polyester into its constituent monomers, transferring the depolymerized products from the reactor to the rectifier, and separating the depolymerized products in the rectifier into a vapor phase containing component monomers and a liquid phase containing higher molecular weight materials.

U.S. Pat. No. 5,576,456 discloses an improvement to the process disclosed in U.S. Pat. No. 5,298,530 in that the reactor for depolymerizing the polyester into its components uses a staged column reactor for the depolymerization and for separating monomer components from the higher boiling materials. The process further utilizes a reactor in which the continuous phase is the super-heated methanol in the molten polyester and polyester decomposition products are the discontinuous phase.

U.S. Pat. No. 5,679,848 discloses a method for making TPA from pure DMT and/or a DMT intermediate product using a counter-current reactor and stripping steam and water under the specific conditions. The DMT is prepared by oxidation of paraxylene and para-toluic acid methyl ester. The method includes the hydrolysis of the DMT in a counter-current reactor and crystallizing the TPA produced without washing it in a subsequent step.

A problem with the all of the above processes for recycling polyester and particularly PET is that the recovered material must be in the form of dimethyl terephthalate (DMT) and ethylene glycol. The reason for this is that DMT, which is reacted with ethylene glycol to form diglycol terephthalate which is then polycondensed to form PET, can be purified using techniques, such as distillation and crystallization, known to those skilled in the art.

Thus, there is a need for a simple and economical method that will permit the recycling of polyesters for recovering suitable feedstock material that may be used in a terephthalic acid (TPA) based polyester manufacturing process.

SUMMARY OF THE INVENTION

Briefly, the present invention provides a process for recovering high quality TPA from recycled polyester, and preferably PET, which may thereafter be used in the manufacture of polyester. In one embodiment of the invention the process includes the step of hydrolyzing a DMT containing material derived from recycled polyester to produce TPA.

In another embodiment of the invention, the process includes the steps of depolymerizing the recycled polyester into a product having component monomers, oligomers, half-esters and DMT; substantially segregating the DMT; and hydrolyzing the DMT to form TPA.

In another embodiment, the process includes the steps of contacting the recycled polyester with monomers and oligomers of the same monomers as present in the recycle polyester to produce a solution or melt; contacting the solution with a super-heated lower alkyl alcohol to depolymerize the polyester into a product having monomers, oligomers of the ester, DMT, and half-esters; substantially segregating the DMT; and hydrolyzing the DMT to form TPA and recovering the TPA.

The apparatus used to carry out the process of the present invention is similar to that used in the process described in the copending patent application having U.S. Ser. No. 09/167,248 entitled "Depolymerization Process for Recycling Polyesters" filed on Oct. 6, 1998, the disclosure of which is incorporated herein by reference, except that the present invention employs a hydrolysis reactor, and preferably a counter-current reactor where the DMT is introduced at a point that is above the location where water and preferably, steam, is introduced into the reactor. Accordingly, an apparatus for practicing the process of the present invention includes a depolymerization reactor, a separator means for substantially segregating DMT from other materials such as ester monomers, oligomers and half-ester products produced from the depolymerization reactor, and a second reactor operated under hydrolysis conditions for forming TPA from the DMT. It is to be understood that although expressed singularly, it is within the scope of the invention described herein that additional reactors and separators may be used to produce the TPA.

In a preferred embodiment, the apparatus includes a dissolver for at least partially solubilizing or forming a melt of the solid polyester prior to feeding the polyester to the depolymerization reactor.

It has now been found that it is possible to prepare TPA from recycled polyester and particularly PET as compared to the previous methods disclosed in the prior art. This latter step of hydrolyzing the DMT, advantageously and unexpectedly, produces relatively high quality TPA from a recycled polyester material using fewer pieces of expensive distillation and separation equipment.

It is to be understood that the embodiments described herein are for illustrative purposes only and inventive concept is not to be considered limited thereto.

DETAILED DESCRIPTION OF THE INVENTION

The feedstock for the process of the invention can be any polyester waste, which, for example, may be post-consumer material, scrap from polyester resin production processes, scrap from processes that form polyester articles, polyester articles rejected because they do not meet specifications, and mixtures thereof. Moreover, the post-consumer polyester treated in accordance with the process of the present invention may contain contaminants originating from the manufacturing of the end article or from goods stored in or used with the polyester article. Typically, such contaminants are deleterious in the recycling of the polyester and should be removed to achieve high quality TPA from the recycled polyester. Examples of such contaminants effectively removed using the process of the invention include aluminum, sand, paper, glue, and chemicals and residues absorbed from materials stored in the container.

For purposes of describing the present invention, the depolymerization and production of TPA from PET is described. However, it will be apparent to one skilled in the art that the process is suitable for other polyesters. For example, polymers that are particularly useful in this process besides PET include PEN, mixtures and copolyesters of PET and PEN as well as copolyesters containing up to about 50 mole % of modifying dibasic acids and/or glycols and blends thereof. Modifying dibasic acids may contain from about 2 to about 40 carbon atoms and include isophthalic, adipic, glutaric, azelaic, sebacic, fumaric, cis- or trans-1,4-cyclohexanedicarboxylic, the various isomers of naphthalene dicarboxylic acids and mixtures thereof. Highly useful naphthalene dicarboxylic acids include the 2,6-, 1,4-, 1,5-, or 2,7-isomers but the 1,2-, 1,3-, 1,6-, 1,7-, 1,8-, 2,3-, 2,4-, 2,5-, and/or 2,8-isomers may also be used. The dibasic acids may be used in acid form or as their esters such as the dimethyl esters for example.

Typical modifying glycols may contain from about 3 to about 10 carbon atoms and include propylene glycol, 1,3-propanediol, 1,4-butanediol, 1,6-hexanediol, diethylene glycol, 1,4-cyclohexanediol, 1,4-cyclohexanedimethanol, neopentyl glycol and the like. The 1,4-cyclohexanedimethanol may be in the cis or the trans form or as cis/trans mixtures.

Figure 1:
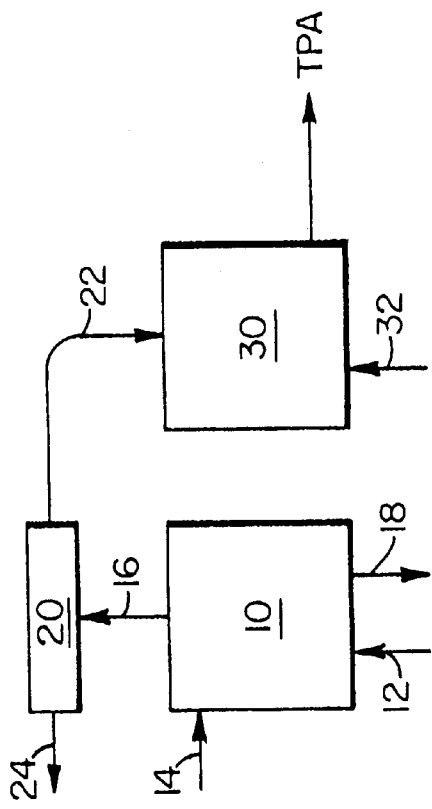
FIG. 1 is a schematic diagram illustrating the process of the present invention.

FIG. 1 is a schematic illustration of a preferred apparatus for carrying out the process of the invention, which may be carried out continuously, semi-continuously, or in a single batch operation. The apparatus includes a depolymerization reactor 10, a rectifier 20, and a hydrolysis reactor 30. The various components of the apparatus are connected together by pipes, pumps, storage tanks, and valves (not shown) as needed to transfer the reactants from one location to another in accordance with the process. The apparatus can further include scrubbers, condensers, reboilers, and the like (not shown) known to those skilled in the distillation art.

In the preferred embodiment, recycle polyester 14, in an appropriate size, is fed to the depolymerization reactor 10 by any suitable means including, but not limited to, pressurization, gravity feed, rotary feed, or from an extruder. The polyester can be a solid material having an average size ranging from a few microns, such as a powder, to the size of a flake having an average size of less than about 1 inch. The polyester may also be fed to the depolymerization reactor 10 as a melt. The depolymerization reactor 10 may be a staged column and can include packing or trays over which the PET is distributed, thereby increasing the surface area that can come in contact with the depolymerization agent, preferably a lower alkyl alcohol. A thin film or wiped film reactor may also be employed and still obtain the operational advantages of this invention. Typically, in a continuous operation such as in a staged column, the polyester is added toward the top of the depolymerization reactor 10 and gravitates toward the bottom.

Alternatively, the depolymerization reactor 10 may be a vessel having an agitator, a temperature control means, such as, a steam jacket or other thermal transfer medium that are well known in the art, and a means for contacting a lower alkyl alcohol, with the recycled polyester to depolymerize the polyester. An example of such a reactor is described in U.S. Pat. No. 5,051,528, the entire disclosure of which is incorporated herein by reference.

A lower alkyl alcohol 12 is added to the depolymerization reactor 10 to depolymerize the PET. Suitable lower alkyl alcohols include methanol, ethanol, propanol and mixtures thereof, with methanol being preferred. When the lower alkyl alcohol 12 is methanol, it is added to the reactor in an amount of from about 0.33 parts by weight to about 10 parts by weight methanol per part of polyester and more preferably, from about 2 parts by weight to about 6 parts by weight methanol per part of polyester, and most preferably, from about 3 parts to about 5 parts by weight methanol per part of polyester.

The methanol 12 may be introduced to the depolymerization reactor 10 as a superheated vapor or as a liquid. The methanol 12 is introduced to the depolymerization reactor 10 using conventional means known to those skilled in the art. Desirably, the super-heated methanol is introduced at or near the bottom of the reactor in sufficient quantities to fill the column and form a continuous vapor phase in the reactor 10 through which the polyester melt descends.

The depolymerization reactor 10 is run under conditions that will maintain the methanol vapor as the continuous phase and substantially provide for complete depolymerization of the polyester 14. The depolymerization reactor 10 is operated under a temperature of about 220° C. to about 300° C. and preferably, from about 240° C. to about 300° C. The temperature of the methanol 12 fed to the depolymerization reactor 10 can range from about ambient temperature to about 300° C., and desirably, ranges from about 200° to about 300° C. and preferably is a super-heated vapor at a temperature of from about 240° C. to about 300° C. The operating pressure of the depolymerization reactor 10 can range from about atmospheric up to about 80 bar and preferably up to about 10 bar.

An ester-exchange catalyst may be added in suitable amounts to the depolymerization reactor 10 to speed the depolymerization reaction. Such catalysts are well known in the art and include compounds of manganese, zinc, titanium, lithium, magnesium, calcium, or cobalt.

A purge stream 18 may be included on the depolymerization reactor 10 to remove nonvolatile components such as high boiling impurities and reaction by-products. Depending on the specific composition of this purge stream 18, it can be discarded, recycled or sent to an additional process for recovery of specific components.

A reboiler (not shown) may optionally be provided at the bottom of the depolymerization reactor 10 to provide heat energy to the depolymerization reactor 10. In one embodiment, the reactor melt can be withdrawn toward the bottom of the reactor, heated and reintroduced toward the top of the reactor.

The depolymerization reactor product stream 16 exits the depolymerization reactor 10 and is transferred to the rectifier 20. The product stream 16 can include such materials as dicarboxylic acid esters, lower alkyl alcohols such as methanol, glycols such as ethylene glycol, diethylene glycol, and triethylene glycol, dimethyl terephthalate, dimethylisophthalate, cyclohexanedimethanol, and methyl-hydroxyethyl terephthalate (MHET). Depending upon the operation of the depolymerization reactor 10, the product stream 16 may be vaporous, liquid or a combination thereof. The rectifier 20 separates the higher boiling secondary materials from the lower boiling materials in the product stream 20. As used herein the term "secondary materials" means materials less volatile than the monomers, methanol, and half-esters and includes, by way of non-limiting example, colorants, dyes, catalyst metals and other higher molecular weight oligomers.

The rectifier product stream 22 generally includes dimethyl esters of the dicarboxylic acid or acids from which the polyester is composed, component monomers and "half-esters", such as methyl hydroxyethyl terephthalate. Desirably, methanol, glycols, MHET and other materials are substantially separated from the DMT. As used herein, "substantially separated" means having greater than about 50 weight % DMT, and preferably greater than 80 weight % DMT and more preferably greater than about 90 weight % DMT and most preferably greater than about 99 weight % DMT. Techniques for separating the various components of the product stream 16 are well known to those skilled in the distillation art. A series of two or more rectifies may also be used in a manner which preferentially separates methanol, glycols and DMT from the product stream 16. A majority of the methanol removed from the rectifier may be returned to the depolymerization reactor 10 via line 24 to conserve methanol and improve raw material efficiencies. The rectifier product stream 22 is kept above the temperature at which DMT will solidify from the solution, generally above about 165° C. to about 210° C. and at a pressure of from about atmospheric to about 10 bar.

Ethylene glycol and other glycols and esters, which boil lower than the DMT, are preferentially stripped from the DMT. Although hydrolysis can be done in the presence of ethylene glycol and other lower boiling components, these components will be in solution in the excess water following hydrolysis, and separation of ethylene glycol from DMT prior to hydrolysis is preferred to removal of the excess water from the ethylene glycol. Also, if glycols and other alcohols are present during the hydrolysis, they will compete with the water and conversion will not be as complete. The ethylene glycol and other low boilers are stripped in distillation equipment using techniques well known to those skilled in the art. The ethylene glycol may be stripped between 0.01 and 100 atmospheres pressure, depending upon equipment and heat source availability.

Molten, stripped DMT is mixed with water and fed to a hydrolysis reactor 30. The hydrolysis reactor 30 may be a counter-current reactor wherein the DMT is introduced above the location where the water 32, preferably steam, is introduced. In a preferred embodiment the steam 32 is introduced at the bottom of the hydrolysis reactor 30. The hydrolysis reactor 30 is generally operated at a temperature higher than the melting point of DMT, about 150° C., but less than the temperature at which significant DMT degradation occurs, usually about 380° C. and at a pressure sufficient to maintain a liquid phase in the bottom of the hydrolysis reactor 30. Desirably, the hydrolysis reactor 30 is operated at a temperature of about 200° C. to about 290° C. and a pressure of about 17 bar to about 100 bar. The pressure is essentially the vapor pressure of water at the temperature selected.

Alternatively, the hydrolysis reactor 30 may be a staged reactor or operated as a series of vessels to reduce back mixing and effect a higher conversion. Regardless of the physical configuration of the hydrolysis reactor 30, certain techniques known to those skilled in the art may be used to drive the methyl ends conversion to completion. The methyl ends conversion will normally be close to 100 per cent, but subsequent polycondensation applications may not require complete methyl ends conversion, in which case the methyl ends conversion may advantageously be significantly less that 100 per cent.

Based on weight, the amount of water added to the hydrolysis reactor 30 is from about 0.19:1 water to DMT, preferably from about 1:1 to about 6:1 water to DMT, and more preferably from about 2:1 to about 4:1. Desirably, vapors which primarily comprise a methanol/water mixture are removed from the reactor and condensed.

It may be desirable to add a hydrolysis catalyst to the reactor to speed the hydrolysis. These catalysts are well known in the art and include compounds of Zn, Mn, Ti, Sn, and Mo. The reaction is run with a residence time adequate to achieve the desired conversion with the temperature and catalyst system chosen, and may be between about 0.1 and about 10 hours.

Terephthalic acid is obtained as the hydrolysis reaction product in the bottom of the hydrolysis reactor 30. The TPA is crystallized in a single or multi-stage crystallization process. The TPA obtained in the crystallization step can be separated from the aqueous materials by process known to those skilled in the separation art. For example, the TPA crystals may be filtered using belt filters, drum filters, pressure filters, centrifuges, single or multi-stage decantation, and the like. The water separated off may be recycled to the hydrolysis reactor 30. In one aspect of the invention, the solid TPA crystals are washed with fresh water which subsequently is used as feed water to the hydrolysis reactor 30.

The high purity TPA solids may be used in a polycondensation reaction wet, but drying will often be desirable to facilitate storage, transport and feeding of the material to the polycondensation reactor. Any type of batch or continuous dryer known to those skilled in the art to be effective for drying water-wet granular solids may be selected.

It is within the scope of the invention to provide a process for the production of TPA by hydrolyzing a DMT containing polyester wherein the polyester includes from about 10 weight % to, preferably, substantially 100 weight % DMT. The polyester feed material and hydrolyzing operation are as described above.

Figure 2:
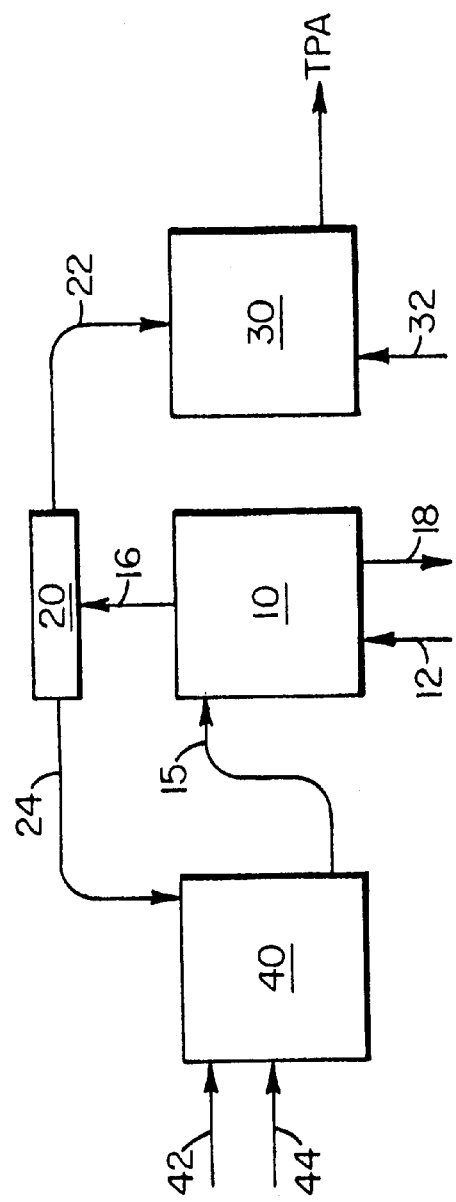
FIG. 2 is a schematic diagram of another embodiment of the process.

Referring to FIG. 2, another embodiment of the invention is illustrated wherein depolymerization includes adding polyester 42 to a dissolver 40 for at least partially solubilizing the polyester 42 prior to its introduction into the depolymerization reactor 10. The recycled polyester 42 is fed to dissolver 40 and is contacted with monomers and oligomers 44 of the same component monomers as the polyester to at least partially solubilize the polyester 42. In the case where the polyester is PET, the monomers and oligomers would be those of ethylene glycol, terephthalic acid and may optionally contain dimethyl terephthalate, with ethylene glycol being preferred. In the dissolver 40, desirably, the PET is solubilized and heated so that the dissolver melt 15 can be fed to the depolymerization reactor 10. Relative to atmospheric pressure, the dissolver 40 can be run at a negative pressure, equal pressure, or at a slightly positive pressure. The dissolver 40 is equipped with a means for heating its contents to a temperature of about 210° C. to about 260° C. and preferably, from about 240° to about 260° C.

Optionally, an ester exchange catalyst, such as zinc acetate, can be added to the dissolver 40. If so included, the amount of catalyst added, based on the metal cation, ranges from about 30 ppm to about 300 ppm, and preferably, from about 30 ppm to about 100 ppm relative to the amount of polyester added to the dissolver 40.

The polyester melt in the dissolver 40 can be protected from the atmosphere by a blanket of inert gas. Suitable inert gases include those gases which do not react with the polyester melt and include nitrogen, carbon dioxide, argon, etc. This reduces degradation of the dissolver melt 15 due to oxidation reactions.

Low boiling components which evolve from the dissolver 40 may contain monomers that can be recovered together with the monomers exiting the depolymerization reactor 10. This can be accomplished by recovering them in a separate process or apparatus or absorbing them into the liquid glycol added to the dissolver 40.

The polyester melt from the dissolver 40 is transferred to the depolymerization reactor 10 via means that can be used to control the rate of introduction of these materials. The depolymerization reactor 10 can be run at a higher pressure than the dissolver 40, which eliminates the need for additional pumps. In an optional embodiment (not shown), a portion of the reactor melt from the depolymerization reactor 10 is returned to the dissolver 40.

Optionally, a portion of the liquid from the rectifier 20 can be sent back to the dissolver 40. While the rectifier 20 is shown as a separate apparatus, one skilled in the art will understand that the rectifier 20 may comprise additional stages of the depolymerization reactor 10 above the point at which dissolver melt 15 is added.

The example which follows is given to better illustrate the inventive concept without in any way limiting it. All parts are given in weight percentages unless specified otherwise.

EXAMPLE

Approximately 200 grams of post-consumer PET flake having about 50 weight % green flake was mixed with 400 grams of methanol. Based on the weight of PET, a sufficient amount of zinc acetate catalyst solution was added to the mixture to bring the concentration of zinc to 200 ppm. The reactants were mixed in a 1 liter autoclave and heated to a temperature of about 240° C. for 2 hours. The pressure in the autoclave was generated by the pressure of the methanol at that temperature. The depolymerized PET was transferred to a distillation flask and heated. The reaction mixture was boiled and DMT, ethylene glycol, and methanol vapors were removed through a rectifying column to condense and collect a ethylene glycol and DMT distillate mixture. The mixture was analyzed as having 70.5 weight % DMT, 19.4 weight % ethylene glycol, and 0.15 weight % diethylene glycol.

A second mixture was prepared by adding together 500 grams of demineralized water with 101.1 grams of the distillate mixture from the rectifying column. The second mixture was heated in a titanium rocking autoclave to 240° C. for 2 hours without additional catalyst. After 2 hours, the product was analyzed as having 90.2 weight % TPA, 9.5 weight % methyl hydrogen terephthalate, and 0.45 weight % DMT. The conversion was less than complete since no effort was made to sweep the methanol from the reactants and the ethylene glycol was not removed before hydrolysis. The color of the product (L*=97.7, a*=0.1, b*=2.8) is acceptable for the preparation of quality PET for container plastic.

Although the present invention is described in terms of the presently preferred embodiment, it is to be understood that such disclosure is not to be interpreted as limiting to the invention described herein. No doubt that after reading the disclosure and studying the figure of drawing, various alterations and modifications will become apparent to those skilled in the art to which the invention pertains. It is intended that the appended claims be interpreted as covering all such alterations and modifications as fall within the spirit and scope of the invention.

What is claimed is:

1. A process for recycling polyester and producing polyester feedstock material from the recycled polyester, said process comprising the steps of:
    a) depolymerizing said recycle polyester into a product having component ester monomers, esters and oligomers of said polyester;
    b) substantially segregating said ester in said depolymerized product; and
    c) hydrolyzing said segregated ester to form a solid polyester feedstock material.

2. The process of claim 1 wherein said depolymerization step includes contacting said recycled polyester with a lower alkyl alcohol selected from the group consisting of methanol, ethanol, propanol and mixtures thereof.

3. The process of claim 1 further comprising contacting said recycle polyester with a solubilizing material selected from monomers and oligomer of the same monomers as present in said recycle polyester to produce a melt.

4. The process of claim 1 wherein said recycle polyester is selected from the group consisting of PET, PEN, mixtures and copolyesters of PET and PEN, copolyesters containing up to about 50 mole % of modifying dibasic acids and/or glycols and mixtures thereof.

5. The process of claim 2 wherein said lower alkyl alcohol is super-heated.

6. The process of claim 3 wherein said recycle polyester is contacted with a solubilizing material selected from the group consisting of glycol, DMT, TPA, methanol and mixtures thereof to at least partially dissolve said polyester.

7. The process of claim 1 wherein said recycle polyester is PET and said segregated ester is DMT.

8. The process of claim 4 wherein said modifying dibasic acid has from 2 to 40 carbon atoms.

9. The process of claim 8 wherein said modifying dibasic acids are selected from the group consisting of isophthalic, adipic, glutaric, azelaic, sebacic, fumaric, dimer, cis- or trans-1,4-cyclohexanedicarboxylic, isomers of naphthalenedicarboxylic acids selected from the group consisting of 2,6-, 1,4-, 1,5-, 2,7-, 1,2-, 1,3-, 1,6-, 1,7-, 1,8-, 2,3-, 2,4-, 2,5-, 2,8-isomers, and dimethyl esters thereof.

10. The process of claim 7 wherein said glycol has from 3 to 10 carbon atoms.

11. The process of claim 10 wherein said glycol is selected from the group consisting of propylene glycol, 1,4-cyclohexanedimethanol, 1,6-hexanediol, diethylene glycol, 1,3-propanediol, 1,4-butanediol, 1,4-cyclohexanediol, and mixtures thereof.

12. The process of claim 7 wherein hydrolyzing DMT forms TPA.

13. The process of claim 12 further comprising crystallizing said TPA.

14. The process of claim 13 wherein said crystallized TPA is recovered.

15. A process for producing TPA from recycled PET comprising the steps of:
    a) depolymerizing said recycle PET into a product comprising DMT;
    b) substantially segregating said DMT from secondary materials; and
    c) hydrolyzing said DMT to form TPA.

16. The process of claim 15 wherein said hydrolyzing step includes contacting said DMT with water in an amount, based on weight, of from about 0.19:1 to about 6:1 water to DMT.

17. The process of claim 15 wherein said hydrolyzing step includes contacting said DMT with water in an amount, based on weight, of from about 2:1 to about 4:1 water to DMT.

18. The process of claim 15 further comprises crystallizing and recovering said TPA from said hydrolysis reactor.

19. A process for producing TPA from recycled PET comprising the steps of:

a) at least partially dissolving said recycled PET using monomers and oligomers of the same component monomers as present in the recycled PET to produce a solution;
b) transferring said solution to a depolymerizing reactor and contacting said solution with methanol under depolymerization conditions to produce DMT;
c) substantially segregating said DMT from secondary materials;
d) hydrolyzing said DMT to form TPA; and
e) recovering said TPA.

20. The process of claim 19 wherein said monomers and oligomers are selected from the group consisting of ethylene glycol, terephthalic acid, and DMT.

21. The process of claim 19 wherein said hydrolyzing step includes contacting said DMT with water in an amount, based on weight, ranging from about 2:1 to about 4:1 water to DMT whereby crystals of TPA are formed and said process further comprises recovering said crystals.

22. A process for producing TPA from a DMT containing material having from about 10 weight % to substantially 100 weight % DMT, said process comprising hydrolyzing said DMT containing material with water in an amount, based on weight, ranging from about 2:1 to about 4:1 water to DMT whereby crystals of TPA are formed.

23. The process of claim 22 wherein said DMT containing material is selected from the group consisting of PET, PEN, mixtures and copolyesters of PET and PEN, copolyesters containing up to about 50 mole % of modifying dibasic acids and/or glycols and mixtures thereof.

* * * * *